(12) United States Patent
Chicco

(10) Patent No.: US 8,952,012 B2
(45) Date of Patent: Feb. 10, 2015

(54) INHIBITION OF DELTA-6 DESATURASE FOR THE TREATMENT OF CARDIOMETABOLIC DISEASE

(71) Applicant: Colorado State University Research Foundation, Fort Collins, CO (US)

(72) Inventor: Adam J. Chicco, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/902,435

(22) Filed: May 24, 2013

(65) Prior Publication Data

US 2013/0317039 A1 Nov. 28, 2013

Related U.S. Application Data

(60) Provisional application No. 61/651,369, filed on May 24, 2012.

(51) Int. Cl.
| | | |
|---|---|---|
| *C12Q 1/26* | (2006.01) | |
| *A01K 67/027* | (2006.01) | |
| *A61K 31/00* | (2006.01) | |
| *G01N 33/68* | (2006.01) | |

(52) U.S. Cl.
CPC ............. *C12Q 1/26* (2013.01); *A01K 67/027* (2013.01); *A61K 31/00* (2013.01); *G01N 33/6893* (2013.01); *G01N 2500/00* (2013.01); *G01N 2800/04* (2013.01); *G01N 2800/32* (2013.01)
USPC .............................. 514/253.01; 435/25; 800/9

(58) Field of Classification Search
CPC ....... C12Q 1/26; A01K 67/027; A01K 31/00; G01N 2800/32; G01N 2500/00; G01N 2800/04; G01N 33/6893
See application file for complete search history.

(56) References Cited

U.S. PATENT DOCUMENTS

| 2004/0096435 A1 | 5/2004 | Winther et al. |
| 2008/0318909 A1 | 12/2008 | Sparagna et al. |

FOREIGN PATENT DOCUMENTS

| WO | WO-00/53770 | * | 9/2000 |

OTHER PUBLICATIONS

Chicco et al. Circ Res. 2009;105(7)e34. Abstract P126.*
Dong et al., Journal of Endocrinology 2006, 188:25-36.*
PCT/US13/42696 International Search Report and Written Opinion (10 pages) mailed Jan. 10, 2014.
Martinelli et al.; "FADS Genotypes and Desaturase Activity Estimated by the Ratio of Arachidonic Acid to Linoleic Acid Are Associated With Inflammation and Coronary Artery Disease"; American Journal of Clinical Nutrition; 2008; vol. 88; pp. 4941-4949.
Obukowicz et al.; "Novel; Selective delta6 or delta5 Fatty Acid Desaturase Inhibitors as Antiinflammatory Agents in Mice"; Journal of Pharmacolgly and Experimental Therapeutics; 2008; vol. 287; No. 1; pp. 157-166.
Abdeen et al.; "Nonalcoholic Steatohepatitis and the Cardiometabolic Syndrome"; JCMS Winter; 2006; pp. 36-40.
Winzell et al.; A Model for Studying Mechanisms and Treatment of Impaired Glucose Tolerance and Type 2 Diabetes; Diabetes; 2004; vol. 53 Suppl. 3; pp. S215-S219.
Matsuzaka et al.; Dual Regulation of MouseD5- and D6-desaturasegene Expression by SREBP-1 and PPAR-alpha; Journal of Lipid Research; 2002; vol. 43; No. 107; pp. 107-114.

* cited by examiner

*Primary Examiner* — Doug Schultz
(74) *Attorney, Agent, or Firm* — Polsinelli PC

(57) ABSTRACT

Systems and methods for screening whether a candidate compound inhibits delta-6 desaturase activity are disclosed. Also disclosed is a transgenic mammal which overexpresses a gene encoding delta-6 desaturase and an animal model of a cardiometabolic disorder or disease that includes the transgenic mammal. A method of treating a cardiometabolic disorder or disease is also disclosed.

8 Claims, 13 Drawing Sheets

INHIBITION OF DELTA-6 DESATURASE FOR THE TREATMENT OF CARDIOMETABOLIC DISEASE

GOVERNMENTAL SUPPORT

This invention was made with government support under Grant No. R21 HL094890 awarded by the National Institutes of Health. The government has certain rights in the invention.

CROSS-REFERENCE TO RELATED APPLICATIONS

This application is a non-provisional of U.S. Provisional Application Ser. No. 61/651,369 filed on May 24, 2012 and entitled "Inhibition of Delta-6 Desaturase for the Treatment of Cardiometabolic Disease", the disclosure of which is hereby incorporated by reference in its entirety.

FIELD OF THE INVENTION

The present disclosure relates to systems and methods for screening whether a candidate compound inhibits delta-6 desaturase activity.

BACKGROUND OF THE INVENTION

The growing prevalence of obesity and type 2 diabetes complicates risk and clinical management by potentiating and/or exacerbating hypertension, hyperlipidemia, atherosclerosis and cardiomyopathy, leading to increasing use of the term "cardiometabolic disease" (CMD) to encompass the many facets of this complex syndrome. While several classes of drugs have been developed to manage various aspects of CMD, novel integrative therapies that target central "unifying" features of its pathogenesis and/or progression are needed to simplify clinical management, reduce risk of multi-drug interactions, and avoid potentially adverse effects, such as the effect of treatment using statin cardiovascular drugs on diabetes risk.

CMD and related disorders are thought to be associated with dietary factors. Compared to the diet of our ancestors, the modern Western diet is highly enriched with linoleic acid (LA), an essential polyunsaturated fatty acid (PUFA), due largely to increased consumption of LA-rich vegetable oils used in commercial food processing. This greater proportion of LA may contribute to the higher prevalence and onset of insulin resistance/type 2 diabetes in developed societies by increasing endogenous production of arachidonic acid (AA) and its proinflammatory eicosanoid derivatives that are key initiators and propagators of inflammatory signaling linked to the development of these conditions. However, numerous large cohort studies examining the effect of dietary n6 PUFA (LA) intake on insulin sensitivity have produced widely variable results, making unclear whether to increase, decrease, or ignore dietary intake of LA in attempting to manage metabolic risk.

Systemic low-grade inflammation is widely believed to play an important role in the pathogenesis and/or progression of all CMD-related pathologies. As described previously, excess dietary LA is thought to increase the endogenous production of arachidonic acid (AA). The metabolism of AA by cyclooxygenase (COX) and lipoxygenase (LO) enzyme pathways generates an array of pro-inflammatory eicosanoid species that are known to be centrally involved in the initiation and propagation of the inflammatory cascade. Accordingly, nearly all currently available treatments for inflammation, such as NSAIDs, target COX enzyme pathways which produce pro-inflammatory eicosanoid species such as prostaglandins and thromboxanes. AA-derived eicosanoid products of the LO enzyme pathways, such as leukotrienes and HETEs, also contribute significantly to inflammatory signaling and are implicated in cardiovascular disease, which has led to the development of several experimental LO and dual COX-LO inhibitor compounds. However, there is some concern regarding the use of these and other inhibitors of AA metabolism enzymes, as different selectivities and potencies of an inhibitor for one enzyme pathway may divert AA into another pathway, creating an imbalance in the relative distribution of species with different, or even opposing, pathogenic potentials. Therefore, the targeting of select AA metabolism enzymes as an anti-inflammatory treatment in metabolic disease and its complications is thought to be a complicated and risky approach.

Delta-6 desaturase (D6D) is a microsomal enzyme that catalyzes rate-limiting steps in the endogenous conversion of dietary LA to AA. The D6D pathway is the primary source of long-chain PUFAs present in biological membranes in the absence of dietary supplementation, therefore changes in serum and tissue D6D product/substrate ratios (e.g., AA/LA) are commonly used as indices of D6D activity in vivo. A number of epidemiological studies over the past two decades have demonstrated positive correlations between serum AA/LA ratios and CMD-related pathologies, but whether elevations in D6D activity actually cause or potentiate the development of CMD/inflammation cannot be determined from these studies. D6D hyperactivity has been recently linked to common single nucleotide polymorphisms of the D6D gene (fads2) that are strongly associated with increased incidence of type 2 diabetes, coronary artery disease and systemic low-grade inflammation. Therefore, D6D hyperactivity, resulting from a "Western" diet or genetic predisposition, could potentiate CMD by increasing endogenous conversion of dietary LA (the primary PUFA in the modern diet) to AA and its pro-inflammatory derivatives. However, the effectiveness of D6D inhibition at reducing or reversing CMD and related syndromes remains largely unknown.

Therefore, a need exists for a treatment for a cardiometabolic disease or disorder that includes administering an inhibitor of D6D. A need also exists for a method for identifying a compound as an inhibitor of D6D for use as a treatment of a cardiometabolic disease or disorder. Further, a need exists for a transgenic animal characterized by the overexpression of D6D for use in the study of the role of D6D overexpression in the progression of a cardiometabolic disease or disorder.

BRIEF SUMMARY OF THE INVENTION

The present disclosure provides a method for identifying a test compound as a candidate compound for the treatment of a cardiometabolic disease or disorder in a mammal. The method may include contacting a mammalian delta-6 desaturase (D6D) with the test compound and determining the level of D6D activity in the presence of the test compound. A decreased level of D6D activity in the presence of the test compound relative to a level of D6D activity in the absence of the test compound may identify the test compound as a candidate compound for the treatment of a cardiometabolic disease or disorder in a mammal. Contacting the mammalian delta-6 desaturase (D6D) with the test compound may occur in vitro. The method may also include: administering an amount of the candidate compound to a mammal, maintaining the mammal for a time and under conditions sufficient to allow the candidate compound to modify D6D activity in the mammal; determining a first value of at least one index of D6D activity before the administration of the candidate compound to the mammal and a second value for the index of D6D activity after the administration of the candidate compound to the mammal; and comparing the first value and the second value of the index of D6D activity. A reduced second value relative to the first value may indicate that the candidate compound reduces D6D activity in vivo. The index of D6D activity may be selected from blood or serum glucose level, glucose tolerance, blood or serum insulin level, insulin resistance, arachidonic acid/linoleic acid (AA/LA ratio), level of at least one proinflammatory eicosanoid; liver macrophage content, and insulin receptor inactivation (IRS-1 phosphorylation). The index values may be determined from a first tissue measurement and a second tissue measurement taken from a tissue selected from serum, liver, heart and muscle. The mammal may be an animal model of human cardiometabolic disease; a murine model of hyperphagic obesity including a leptin-deficient ob mouse; a murine model of diet-induced insulin resistance including a normal mouse maintained on a fat-enriched ("western") diet for a period of at least about 12 weeks; or a transgenic mouse which overexpresses the fatty acid desaturase 6 (fads2) gene. The disease or disorder involving insulin resistance may be selected from hyperglycemia, type 2 diabetes, metabolic syndrome, hyperlipidemia and oxidative stress.

In another aspect, the present disclosure provides a transgenic knock-in mammal characterized by overexpression of D6D. The transgenic mammal may include a genetically modified genome comprising at least one additional endogenous gene encoding a delta-6 desaturase. The endogenous gene encoding a delta-6 desaturase may be fads2. The transgenic mammal may be a rodent, a mouse, or a rat.

In an additional aspect, the present disclosure provides an animal model for studying a cardiometabolic disease or disorder in a mammal. The animal model may include a mammal having a heterozygous promotion of at least one endogenous gene encoding a delta-6 desaturase. The endogenous gene encoding a delta-6 desaturase may be fads2. The transgenic mammal may be a rodent, a mouse, or a rat. The cardiometabolic disease or disorder may be selected from hyperglycemia, type 2 diabetes, metabolic syndrome, hyperlipidemia and oxidative stress.

In an additional aspect, the present disclosure provides a method for treating a cardiometabolic disease or disorder. The method may include administering to a subject in need thereof a therapeutically effective amount of an inhibitor of delta-6 desaturase (D6D). The inhibitor of D6D may be SC-26196 or a derivative thereof. Administering to the subject may include administration by a route selected from oral, intravenous, subcutaneous, intramuscular, and intraperitoneal administration.

BRIEF DESCRIPTION OF THE DRAWINGS

The following drawings illustrate various aspects of the disclosure.

Corresponding reference characters and labels indicate corresponding elements among the views of the drawings. The headings used in the figures should not be interpreted to limit the scope of the claims.

DETAILED DESCRIPTION

In various aspects, the disclosure provides methods of identifying a test compound as a candidate compound for the treatment of a cardiometabolic disease or disorder in a mammal. Using this method, the candidate compound may be identified as a compound associated with a decreased level of delta-6 desaturase (D6D) activity. In various other aspects, the disclosure provides a method of treating cardiometabolic disease or disorder by administering a therapeutically effective amount of an inhibitor of delta-6 desaturase (D6D) to a subject in need.

Figure 1:
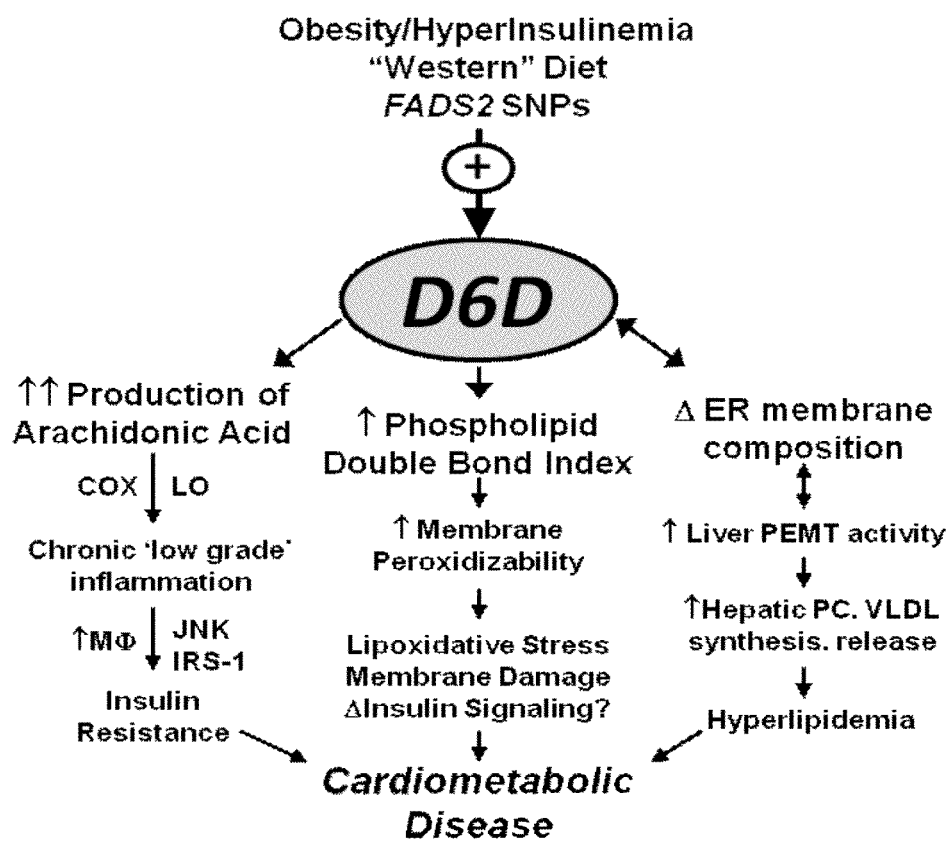
FIG. 1 is a flow chart illustrating the hypothesized role of D6D in cardio-metabolic disease.

Without being limited to any particular theory, it is thought that D6D may have a pivotal role in the development and progress of cardiometabolic disease (CMD) and related symptoms including, but not limited to insulin resistance, chronic inflammation, hyperlipidemia, and lipooxidative stress. A schematic illustration of D6D's role in the etiology of CMD is provided in FIG. 1. D6D is a microsomal enzyme known to catalyze a rate limiting step in the conversion of linoleic acid (LA), a dietary essential polyunsaturated omega-6 fatty acid (PUFA), to arachidonic acid (AA), a polyunsaturated omega-6 fatty acid, as well as proinflammatory eicosanoid derivatives of AA that are key initiators and propagators of inflammatory signaling linked to the development of insulin resistance and type 2 diabetes. The D6D pathway is a primary source of long-chain PUFAs present in biological membranes in the absence of dietary supplementation, and therefore exerts a major influence on phospholipid PUFA composition. The mechanisms by which D6D promotes CMD may include an augmentation of inflammatory signaling through AA metabolism as well as hepatic lipogenesis and export.

D6D enzymatic activity may be assessed using a ratio of product:precursor (serum and tissue AA/LA ratio) as a surrogate marker of systemic D6D activity in vivo; an elevated AA/LA ratio indicates D6D hyperactivity. Over the past two decades, elevated serum AA/LA ratio has been associated with a variety of disorders including, but not limited to: insulin resistance, childhood obesity, impaired fasting glucose, incident type 2 diabetes, development of metabolic syndrome, LDL oxidation in type 2 diabetics, hyperlipidemia and hyperinsulinemia in fatty liver disease. In addition, elevated AA/LA ratio has been shown to independently predict cardiovascular disease (CVD) incidence and mortality.

Although the specific mechanisms by which D6D hyperactivity is associated with this variety of disorders remain to be characterized, D6D hyperactivity has been recently linked to common single nucleotide polymorphisms (SNPs) of the D6D gene (fads2). These fads2 SNPs have been demonstrated to be highly predictive of type 2 diabetes, inflammation and cardiovascular disease. In addition, D6D hyperactivity and/or expression are known to be independently stimulated by hyperinsulinemia as well as dietary factors including excessive dietary sucrose, cholesterol, or hydrogenated fat.

This association of elevated D6D enzymatic activity with a wide variety of metabolic-related disorders, coupled with the linking of D6D hyperactivity with fads2 SNPs, infer that a genetic predisposition for increased D6D activity may potentiate the risk of a variety of diseases associated with inflammation, including diabetes and cardiovascular disease, by enhancing endogenous production of AA and its pathogenic metabolites.

It has been discovered unexpectedly that the inhibition of D6D activity in animal models of cardiometabolic disease (CMD) resulted in widespread and potent reduction and/or reversal of a variety of pathological conditions related to CMD. As described in detail herein below in the Examples, D6D inhibition in murine models of hyperphagic obesity and diet-induced insulin resistance not only reversed elevations in D6D activity indices (e.g., AA/LA ratio) in serum, liver, heart and muscle in these models, but also normalized glucose tolerance and serum levels of several COX and LOX-derived proinflammatory eicosanoids. D6D inhibition also attenuated hepatic inflammation as measured by macrophage content; attenuated insulin receptor inactivation as measured by IRS-1 phosphorylation; and reduced evidence of tissue lipoxidative stress. D6D inhibition in the murine models was also surprisingly found to induce dramatic normalization of tissue membrane phospholipid contents to healthy compositions, which may further provide potent protective effects in the context of CMD.

Without being limited to any particular theory, inhibition of the D6D pathway may attenuate CMD risk by reducing the extent of systemic low-grade inflammation by slowing endogenous AA production and subsequent flux through COX and LO pathways. D6D activity may indeed represent a pivotal determinant of cardiometabolic risk. Therefore, pharmacological inhibition of D6D activity may be a safe and highly effective means of treatment of CMD, as well as a means of further elucidating the mechanisms responsible for the development and progression of CMD and related disorders.

Method of Identifying D6D Inhibiting Compounds

In one aspect, a method of identifying a test compound as a candidate compound for the treatment of a cardiometabolic disease (CMD) or disorder in a mammal is provided. In this aspect, the identified candidate compound may be characterized by its efficacy in inhibiting mammalian delta-6 desaturase (D6D) activity. A variety of assays, both in vitro and in vivo may be used to assess the test compound according to this method, as described in detail herein below. Non-limiting examples of cardiometabolic disease or disorders suitable for treatment using the candidate compounds identified by the methods in this aspect include: insulin resistance, hyperglycemia, type 2 diabetes, metabolic syndrome, hyperlipidemia and oxidative stress.

Figure 2:
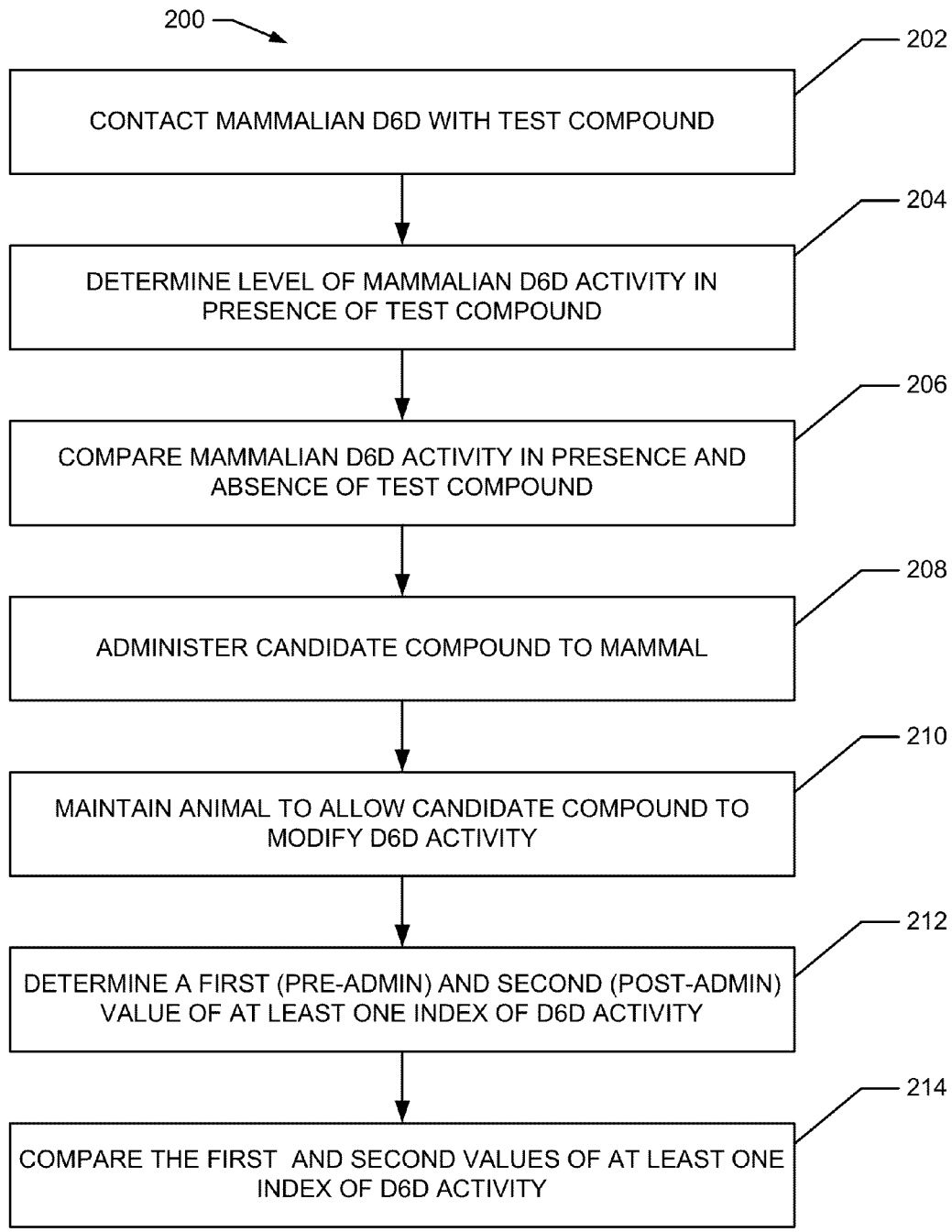
FIG. 2 is a flow chart summarizing a method of identifying a test compound as a candidate compound for the treatment of a cardiometabolic disease or disorder in a mammal.

FIG. 2 is a flow chart summarizing a method 200 of identifying a test compound as a candidate compound for the treatment of a cardiometabolic disease (CMD) or disorder in an aspect. In this aspect, the method 200 may include contacting the test compound with D6D at step 202. Any known method may be used to contact the test compound with the D6D. In various aspects, the test compound may be contacted with the D6D using any known method including, but not limited to a vitro assay, an in vivo assay, and any combination thereof.

The in vitro assay may include, but is not limited to a cell culture and/or a preparation in various aspects. Non-limiting examples of suitable cell cultures include a mammalian liver cell culture, a mammalian muscle cell culture, a mammalian cardiac cell culture, and any combination thereof. Non-limiting examples of suitable preparations include a microsome preparation derived from at least one of: mammalian liver cells, mammalian muscle cells, and mammalian cardiac cells. To obtain the microsome preparation, any standard method known in the art may be used. By way of non-limiting example, mammalian liver cells may be homogenized and centrifuged at least one time. In this example, the supernate may be discarded after centrifuging and the pellet containing the microsomes may be resuspended in a buffer such as a homogenization buffer to form the preparation.

The in vivo assay may include administering an amount of the test compound to a mammal. Any mammal may be suitable for use in the in vivo assay including, but not limited to: mice, rats, rabbits, pigs, dogs, cats, monkeys, cows, horses, and humans. In various aspects, it may be advantageous to conduct an in vivo assay using healthy animal model, an animal model of a CMD, or both. In one aspect, the animal model of a CMD may be a wild-type animal in which a CMD-related condition is induced by dietary means. Non-limiting examples of dietary means suitable for inducing CMD and/or a CMD-related condition include feeding the mammal a diet characterized by a relatively high proportion of LA or other n6 PUFAs, a relatively high proportion of sucrose, and/or any other dietary means of inducing CMD and/or a CMD-related condition.

By way of non-limiting example, an animal model of a CMD may be a wild-type animal or other suitable genotype chronically fed a diet that includes about 20% lard by weight for a period of at least 8 weeks prior to participation in any experimental manipulations or measurements. Typically, at least 8 weeks is needed before overt metabolic dysfunction is observed in this non-limiting example.

In another aspect, the animal model of a CMD may be a transgenic animal model in which one or more genes associated with CMD or a CMD condition are knocked out, overexpressed, or modified in any other suitable manner known in the art. Non-limiting examples of transgenic animal models of a CMD include: leptin-deficient ob/ob mice, LDL receptor knockout mice, fads2-TG mice, and any other suitable transgenic animal model known in the art.

Referring back to FIG. 2, if an in vitro assay as described herein above is used, an effective amount of the test compound may be added to a nutrient solution of a cell culture, or to a suspension buffer of a microsome preparation at step 202. If an in vivo assay is used, the test compound may be contacted with the D6D at step 202 by administering an effective amount of the test compound to the mammal. The test compound may be administered using any known administration method including, but not limited to: oral administration, intravenous administration, subcutaneous administration, intramuscular administration, intraperitoneal administration, and any combination thereof.

The test compound may be contacted with the D6D for an extended period prior to obtaining any measurements. In various aspects, the amount of time that the test compound is contacted with the D6D should be sufficiently long to allow the test compound to modify D6D activity. In one aspect, if an in vitro assay is used, the test compound may be contacted with the D6D for a time period ranging up to about 24 hours. In other aspects, if an in vitro assay is used, the test compound may be contacted with the D6D for a time period of about 1 minute to about 10 minutes, of about 5 minutes to about 15 minutes, of about 10 minutes to about 20 minutes, of about 15 minutes to about 25 minutes, of about 20 minutes to about 30 minutes, of about 25 minutes to about 35 minutes, of about 30 minutes to about 40 minutes, of about 35 minutes to about 45 minutes, of about 40 minutes to about 50 minutes, of about 45 minutes to about 55 minutes, of about 50 minutes to about 60 minutes, of about 55 minutes to about 65 minutes, of about 1 hour to about 3 hours, of about 1 hour to about 3 hours, of about 2 hours to about 4 hours, of about 3 hours to about 5 hours, of about 4 hours to about 6 hours, of about 5 hours to about 7 hours, of about 6 hours to about 8 hours, of about 7 hours to about 9 hours, of about 8 hours to about 10 hours, of about 9 hours to about 11 hours, of about 10 hours to about 12 hours, of about 11 hours to about 13 hours, of about 12 hours to about 14 hours, of about 13 hours to about 15 hours, of about 14 hours to about 16 hours, of about 15 hours to about 17 hours, of about 16 hours to about 18 hours, of about 17 hours to about 19 hours, of about 18 hours to about 20 hours, of about 19 hours to about 21 hours, of about 20 hours to about 22 hours, of about 21 hours to about 23 hours, and of about 22 hours to about 24 hours.

In another aspect, if an in vivo assay is used, the test compound may be contacted with the D6D for a time period ranging up to about 8 weeks. In other aspects, if an in vivo assay is used, the test compound may be contacted with the D6D for a time period of about 1 hour to about 3 hours, of about 2 hours to about 4 hours, of about 3 hours to about 5 hours, of about 4 hours to about 8 hours, of about 6 hours to about 12 hours, of about 8 hours to about 16 hours, of about 12 hours to about 24 hours, of about 18 hours to about 36 hours, of about 1 day to about 3 days, of about 2 days to about 4 days, of about 3 days to about 5 days, of about 4 days to about 6 days, of about 5 days to about 1 week, of about 6 days to about 2 weeks, of about 1 week to about 3 weeks, of about 2 weeks to about 4 weeks, of about 3 weeks to about 5 weeks, of about 4 weeks to about 6 weeks, of about 5 weeks to about 7 weeks, and of about 6 weeks to about 8 weeks.

Referring back to FIG. 2, the method may further include determining the level of D6D activity in the presence of the test compound at step 204. If an in vitro assay is used as described in one aspect, an amount of linoleic acid (LA) may be introduced into the nutrient solution of a cell culture, or to the suspension buffer of the microsome preparation. The LA may incorporate a radioactive marker including, but not limited to, carbon-14 in order to quantify the amount of LA participating in the enzymatic reaction catalyzed by the D6D. In this aspect the level of D6D activity in the presence of the test compound may be determined by calculating the ratio of AA concentration/LA concentration in the cell nutrient or buffer solution (product:precursor ratio). The AA and LA concentrations may be determined using any method of quantifying enzyme activity known in the art including, but not limited to: chromatographic separation and quantification, antibody-based assays, or any combination thereof.

If an in vivo assay is used, the level of D6D activity may be detected in the mammal after administration of the test compound using any method of quantifying enzyme activity in vivo known in the art without limitation. In one aspect, the level of D6D activity may be detected in the mammal by determining a level of at least one index of D6D activity. Non-limiting examples of suitable indices of D6D activity include: blood or serum glucose level, glucose tolerance, blood or serum insulin level, insulin resistance, arachidonic acid/linoleic acid (AA/LA ratio), dihomo-γ-linolenic acid to linoleic acid ratio (DGLA/LA), 22:6n3/22:5n3 ratio level of at least one proinflammatory eicosanoid; liver macrophage content, and insulin receptor inactivation (IRS-1 phosphorylation). The level of the at least one index of D6D activity may be determined using methods known in the art that are appropriate for the particular index of D6D activity for which a level is to be determined. By way of non-limiting example, if the index of D6D activity to be determined is blood or serum glucose level, the blood or serum glucose level may be determined using any method known in the art including, but not limited to: analysis of a blood or serum sample obtained from the mammal using chemical or enzymatic detection methods, non-invasive glucose monitoring methods such as near-IR detection, ultrasound detection, and dielectric spectroscopy, and any combination thereof.

Referring back to FIG. 2, the method 200 may further include comparing the D6D activity in the presence and absence of the test compound at step 206. In one aspect, a decreased level of D6D activity in the presence of the test compound relative to a level of D6D activity in the absence of the test compound identifies the test compound as a candidate compound for the treatment of a cardiometabolic disease or disorder in a mammal. In one aspect, the comparison of the D6D activity in the presence and absence of the test compound may be performed in step 206 by determining a baseline level of D6D activity using any one or more of the methods described herein above prior to contacting the test compound with the D6D and comparing this baseline level of D6D activity to the level of D6D activity in the presence of the test compound determined in step 204.

In another aspect, the comparison performed in step 206 may be accomplished by comparing the level of D6D activity in the presence of the test compound determined in step 204 to a predetermined threshold level of D6D activity. This predetermined threshold level may be obtained by determining one or more baseline levels of D6D activity in the absence of the target compound using any one or more known methods including, but not limited to: obtaining published baseline levels of D6D reported for similar in vitro or in vivo assays in the scientific literature and measuring and storing a baseline level of D6D activity from one or more in vitro or in vivo assays performed prior to the use of the method 200. In this other aspect, a level of D6D activity in the presence of the test compound that is less than the predetermined threshold value identifies the test compound as a candidate compound for the treatment of a cardiometabolic disease or disorder in a mammal.

Referring again to FIG. 2, the method 200 further includes administering an amount of the candidate compound identified in step 206 to a mammal at step 208. In various aspects, the mammal may be the same mammal species as was used as an in vivo model in steps 202-206 or the mammal may be a different species. Non-limiting examples of suitable mammals for use in step 208 include: mice, rats, rabbits, pigs, dogs, cats, monkeys, cows, horses, and humans.

In various aspects, the mammal may be in a healthy condition, or may be afflicted with one or more CMDs or disorders. In one aspect, the mammal afflicted with a CMD or disorder may be a wild-type mammal that is afflicted with a CMD or disorder of undetermined causation including, but not limited to human patients diagnosed with CMD or other disorder by a medical practitioner. In another aspect, the mammal afflicted with CMD or other disorder may be a mammal induced to develop a CMD or other disorder as described previously herein in connection with in vivo assays. Non-limiting examples of mammals induced to develop a CMD or other disorder include: feeding a wild-type or transgenic mammal a diet known to induce a CMD or other disorder such as a high LA and/or high sucrose diet, as described herein previously; transgenic mammals in which one or more genes associated with CMD or a CMD condition are knocked out, overexpressed, or modified in any other suitable manner as described previously herein.

Other non-limiting examples suitable for use in step 206 include: an animal model of human cardiometabolic disease; a murine model of hyperphagic obesity including a leptin-deficient ob/ob mouse; a murine model of diet-induced insulin resistance including a normal mouse maintained on a fat-enriched ("western") diet for a period of at least about 4 weeks; and a transgenic mouse which overexpresses the fatty acid desturase 6 (fads2) gene.

The method of administration of the candidate compound in step 208 may be accomplished using any known method of active compound administration including, but not limited to: oral administration, intravenous administration, subcutaneous administration, intramuscular administration, intraperitoneal administration, and any combination thereof.

Referring again to FIG. 2, the method 200 may further include maintaining the mammal for a time and under conditions sufficient to allow the candidate compound to modify D6D activity in the mammal at step 210. In one aspect, the mammal may be maintained in step 210 for a time period ranging up to about 8 weeks. In other aspects, the mammal may be maintained in step 210 for a time period of about 1 hour to about 3 hours, of about 2 hours to about 4 hours, of about 3 hours to about 5 hours, of about 4 hours to about 8 hours, of about 6 hours to about 12 hours, of about 8 hours to about 16 hours, of about 12 hours to about 24 hours, of about 18 hours to about 36 hours, of about 1 day to about 3 days, of about 2 days to about 4 days, of about 3 days to about 5 days, of about 4 days to about 6 days, of about 5 days to about 1 week, of about 6 days to about 2 weeks, of about 1 week to about 3 weeks, of about 2 weeks to about 4 weeks, of about 3 weeks to about 5 weeks, of about 4 weeks to about 6 weeks, of about 5 weeks to about 7 weeks, and of about 6 weeks to about 8 weeks.

In various aspects, the conditions under which the mammal may be maintained in step 210 may include maintenance of additional factors including, but not limited to: concentration of the candidate compound, diet, activity of the mammal, wake/sleep cycles, and other miscellaneous environmental conditions. In one aspect, the candidate compound may be administered in a single dosing in step 208 such that the concentration of the candidate compound is maintained above an effective level for a time period sufficient to modify D6D activity in the mammal. In another aspect, the concentration of the candidate compound may be maintained at a relatively constant level by any means known in the art including, but not limited to: continuous administration of the candidate compound using known methods such as continuous intravenous administration; administration of controlled-release compositions including the candidate compound such as extended release oral compositions; and administration of the candidate compound using a implant configured to release the candidate compound with an essentially zero-order release profile. In an additional aspect, the maintenance of the concentration of candidate compound may be maintained according to a predetermined schedule that may vary with time. Non-limiting examples of suitable predetermined schedules include a constantly increasing concentration over time associated with the administration of multiple doses of increasing size and/or frequency; an initial increase followed by a gradual decrease in concentration associated with a single administration; and cycles of increasing and decreasing concentration associated with multiple repeated doses in which the doses may be repeated twice or more daily, daily, every other day, every third day, every fourth day, every fifth day, every sixth day, weekly, every other week, and monthly.

Non-limiting examples of dietary factors that may be maintained in step 210 include: total caloric intake; proportion of overall fat, protein and/or carbohydrate; supplementary dietary factors such as additional LA, vitamins, minerals, and/or medications in addition to the candidate compound; caloric allocation and timing of meals; and any other dietary factor known in the art. Non-limiting examples of factors related to the activity of the mammal include the duration, intensity, frequency, scheduling of exercise, as well as other activities such as spontaneous movement about an enclosure, sitting versus standing, and any other activity-related factor known in the art. Non-limiting examples of other miscellaneous environmental factors include light/dark cycles, ambient temperature and/or humidity, presence or absence of other mammals, and any other relevant miscellaneous environmental factor.

Referring back to FIG. 2, the method 200 may further include determining a first value of at least one index of D6D activity before the administration of the candidate compound to the mammal and a second value for the index of D6D activity after the administration of the candidate compound to the mammal at step 212. Non-limiting examples of suitable indices of D6D activity include: blood or serum glucose level, glucose tolerance, blood or serum insulin level, insulin resistance, arachidonic acid/linoleic acid (AA/LA ratio), level of at least one proinflammatory eicosanoid, liver macrophage content, and insulin receptor inactivation (IRS-1 phosphorylation). In one aspect an index of D6D activity may be a mathematical combination of two or more of the indices of D6D activity discussed previously. In this one aspect, the mathematical combination may include one or more of the indices of D6D multiplied by one or more weighting factors and combined using one or more mathematical operators including, but not limited to: addition, subtraction, multiplication, and division. By way of non-limiting example, a mathematic combination may be a weighted sum of two or more indices of D6D activity, in which each index of D6D activity is multiplied by an individual weighting factor and added together.

The at least one index of D6D activity may be determined using any method known in the art including, but not limited to the methods described herein above in connection with the determination of the level of D6D activity using an in vivo assay at step 204, as well as the methods described herein below in the Examples.

In one aspect, the first value of the at least one index of D6D activity may be determined by obtaining the appropriate measurements from the mammal prior to the administration of the candidate compound. In another aspect, the first value of the at least one index of D6D activity may be determined by retrieving a predetermined threshold value of the index of D6D activity in the absence of the candidate compound. This predetermined threshold value may be obtained by determining one or more baseline values of the index of D6D activity in the absence of the candidate compound using any one or more known methods including, but not limited to: obtaining published baseline levels of D6D reported for similar in vitro or in vivo assays in the scientific literature, and measuring of one or more indices of D6D activity using comparable mammals prior to the use of the method 200 and storing one or more baseline values.

Referring back to FIG. 2, the method 200 further includes comparing the first value and the second value of the at least one indices of D6D activity at step 214. A reduced second value relative to the first value indicates that the candidate compound reduces D6D activity in vivo.

In one aspect, step 214 may be performed a single time using a single second value obtained at a selected time after the initial administration of the candidate compound at step 208. This aspect may correspond to a single administration of the candidate compound, or alternatively may correspond to the maintenance of a predetermined concentration of the candidate compound in the mammal over an extended period of time. In another aspect, additional values of the at least one index of D6D activity may be obtained by repeating step 212 at predetermined intervals after the initial performance of step 212. These additional values at least one index of D6D activity may be compared repeatedly at step 214 to obtain a time profile of the effect of the candidate compound on D6D activity.

Transgenic Mammals Overexpressing D6D

In various other aspects, the disclosure provides a transgenic knock-in mammal characterized by the overexpression of delta-6 desaturase (D6D). In one aspect, the genetically modified genome includes at least one additional endogenous gene encoding a D6D. The transgenic mammal may be any mammal including, but not limited to mice, rats, rabbits, pigs, dogs, cats, monkeys, sheep, cows, and horses. In one aspect, the transgenic mammal may be a rodent including, but not limited to a mouse or a rat.

In an aspect, the at least one additional endogenous gene encoding a delta-6 desaturase is fads2. To produce the transgenic knock-in mammal, the full length fads2 gene may be cloned into a mammalian expression vector that also includes an expression cassette. A purified fragment containing one or more restriction enzymes and the expression cassette may be transfected into a pronuclei of a fertilized mammal to generate the transgenic knock-in animal.

By way of non-limiting example, a full-length mouse Fads2 cDNA sequence may be cloned into the EcoRV and NotI site of the pcDNA-3.1(+) mammalian expression vector, thereby situating the Fads2 downstream of a CMV promoter and upstream of a polyadenylation sequence and a neomycin resistant gene. A purified NruI/Bst1107I fragment containing the CMV-Fads2 expression cassette may be microinjected into the pronuclei of fertilized FVB/N mice to generate the transgenic knock-in mice overexpressing D6D.

In an aspect, the genotype of the transgenic knock-in mammal may be confirmed by comparing the genotype of the candidate transgenic mammal to a corresponding genotype of a non-transgenic wild-type mammal. Any known method of assessing the genotype of the mammals may be used including, but not limited to Southern blot and PCR amplification of genomic DNA. In another aspect, the phenotype of the transgenic knock-in mammal may be compared to the corresponding phenotype of the corresponding wild-type mammal to further confirm the transgenic traits of the transgenic knock-in mammal. The phenotype of the transgenic and wild-type mammals may be compared by measuring any one or more of the indices of D6D activity discussed previously herein including, but not limited to: blood or serum glucose level, glucose tolerance, blood or serum insulin level, insulin resistance, arachidonic acid/linoleic acid (AA/LA ratio), level of at least one proinflammatory eicosanoid; liver macrophage content, and insulin receptor inactivation (IRS-1 phosphorylation).

In another aspect, the founder (F1) generation of transgenic knock-in mammals produced using the procedures described previously may be cross-bred with a corresponding wild-type mammal to assess germline transmission according to standardized procedures well-known in the art. The resulting F2 generation may be back-crossed with the parent F1 generation to assess the consistency and stability of the D6D overexpression trait. Successive generations may be backcrossed and similarly assessed.

In various aspects, the transgenic knock-in mammal is characterized by a number of consistent alterations of phenotypic traits relative to a corresponding wild-type mammal including, but not limited to: increased fasting blood glucose levels; impaired glucose tolerance; increased hepatic AA/LA levels; eicosanoids and PC/PE levels; increased body weight; and hyperlipidemia. AS such, the transgenic knock-in mammal may be used as an animal model for studying a cardiometabolic disease or disorder in a mammal.

In various aspects, an animal model for studying a cardiometabolic disease or disorder in a mammal is provided. In one aspect, the animal model includes a mammal having a heterozygous promotion of at least one endogenous gene encoding a delta-6 desaturase. In another aspect, the endogenous gene encoding a delta-6 desaturase may be fads2. The animal model may be any mammal including, but not limited to mice, rats, rabbits, pigs, dogs, cats, monkeys, sheep, cows, and horses. In one aspect, the animal model may be a rodent including, but not limited to a mouse or a rat. Non-limiting examples of cardiometabolic diseases or disorders suitable for study using the animal model include hyperglycemia, type 2 diabetes, metabolic syndrome, hyperlipidemia and oxidative stress.

In one aspect, the animal model may be used to examine the phenotypic consequences resulting from heterozygous promotion of at least one endogenous gene encoding D6D. In another aspect, the animal model may be used to examine the phenotypic consequences of disrupting D6D activity in a mammal chronically exposed to elevated levels of D6D activity. Since D6D is thought to be involved in a variety of biological, medical or physiological processes or phenomena, including, but not limited to, hyperglycemia, type 2 diabetes, metabolic syndrome, hyperlipidemia and oxidative stress, the animal model having heterozygous promotion of at least one endogenous gene encoding D6D may be useful for studying mechanisms and/or etiology of these processes or phenomena. In an additional aspect, the animal model having heterozygous promotion of at least one endogenous gene encoding D6D will be useful as a mammalian in vivo screening model for studying these and other processes/phenomena.

In another aspect, the animal model may be sufficiently similar to humans in terms of anatomy, physiology, or response to variations in diet, activity, and/or other environmental conditions, as well as response to one or more D6D inhibitory compounds to be used in medical research investigating a physiological or pathological mechanism. In one aspect, the animal model may be an exploratory model, aiming to understand a biological mechanism. In a second aspect, the animal model may be a predictive model in which the animal model is used with the aim of discovering and quantifying the impact of a treatment.

Method of Treating Cardiometabolic Disease Using D6D Inhibiting Compounds

In various aspects, the disclosure provides a method for treating a cardiometabolic disease or disorder. In one aspect, the method includes administering to a subject in need thereof a therapeutically effective amount of an inhibitor of delta-6 desaturase (D6D). In one aspect, the cardiometabolic disease or disorder may be chosen from: insulin resistance, hyperglycemia, type 2 diabetes, metabolic syndrome, hyperlipidemia and oxidative stress. The therapeutically effective amount, as used herein, refers to the dose required to treat a condition or disease including, but not limited to, a cardiometabolic disease or disorder.

Figure 21:
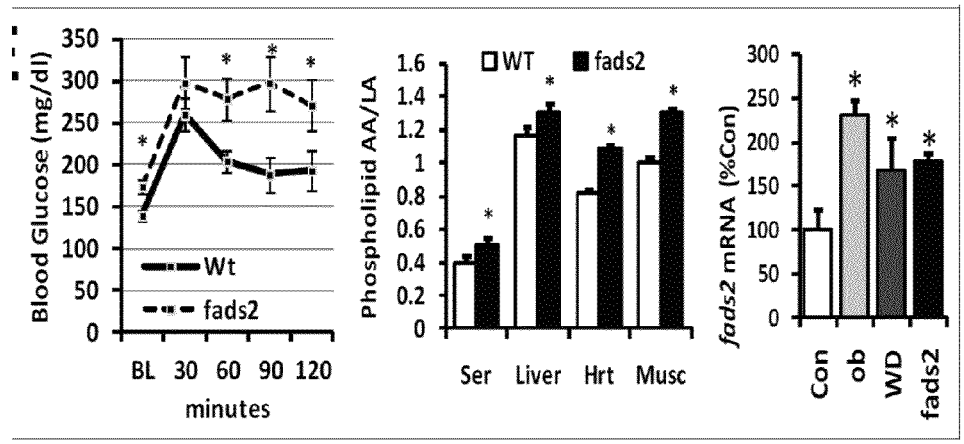
FIG. 21 contains graphs and images illustrating the effect of transgenic overexpression of fads2 on tissue AA/LA ratios and glucose tolerance compared to wild-type (WT) littermates.
Figure 22:
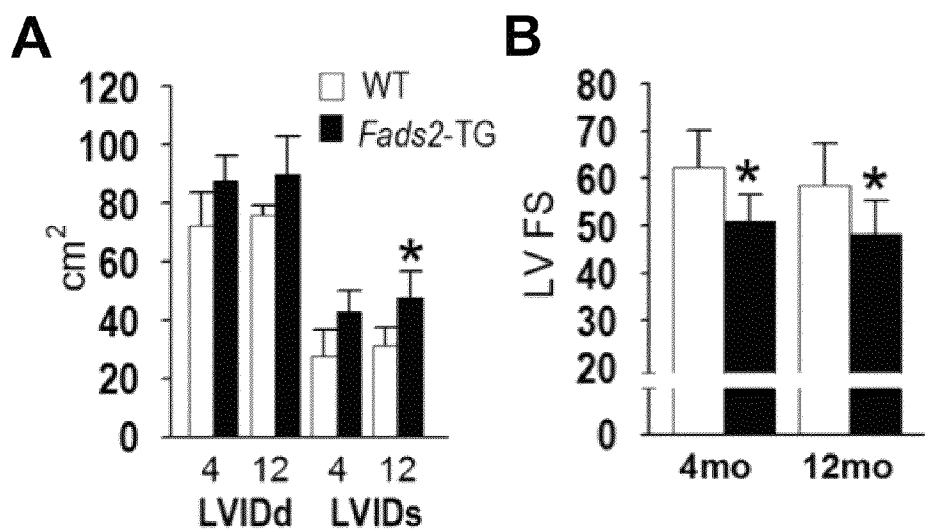
FIG. 22A is a bar graph summarizing LV internal areas in diastole (LVIDd) and systole (LVIDs) obtained using echocardiography of F3 Fads2-TG transgenic mice compared to wild-type (WT) littermates.
FIG. 22B is a bar graph comparing fractional shortening (LV FS) obtained using echocardiography of 4 month old F5 mice and 12 month old F3 mice compared to wild-type (WT) littermates.

In one aspect, the inhibitor of delta-6 desaturase (D6D) may be SC-26196 or a derivative thereof. FIG. 21 is a diagram illustrating the chemical structure of SC-26196, also known as ((E)-2,2-Diphenyl-5-{4-[(pyridin-3-yl-methylene)amino]piperazin-1-yl}pentanenitrile). SC-26196 may exhibit potent selectivity for D6D over other desaturase enzymes with an $IC_{50}$ of 0.2 µM in vitro and oral activity at 100 mpk. In an aspect, SC-26196 or any derivatives thereof may be used to inhibit D6D activity.

At present, SC-26196 is the only known selective D6D inhibitor with oral activity. While we have demonstrated remarkably beneficial effects of this compound in animal models of CMD, as described herein below in the Examples, at least 2 factors may limit the potential therapeutic utility of SC-26196 in humans. In addition, a possible off-target effect of SC-26196 may impact this compound's selectivity and utility as a means of investigating the role of D6D in CMD models.

Initial characterization of SC-26196 showed an $IC_{50}$ of 0.2 µM in vitro and about 65% inhibition of D6D enzymatic activity in vivo at a dose of 100 mg/kg b.i.d., i.g. over a 24 hr period. Chronic administration at 100 mpk/d (mixed in mouse chow) for 4 weeks subsequently reduced tissue AA/LA ratios in mice, and imparted protective effects in a model of acute inflammation. Lower doses (50 and 75 mpk/d, for 4 wks) may be ineffective at reversing the stereotypical elevations of tissue AA/LA associated with acute inflammation, and may further be unable to elicit the same improvements on disease outcomes associated the 100 mpk/d dose. Therefore, potency may be a significant limitation to the use of SC-26196 in humans. Peak plasma levels following 100 mpk ig dosing was 2 µM with a half-life of 1.2 hours and about 60% bioavailability based on AUC calculations, however it is unclear if bioavailability may be further enhanced by modification of its structure.

In addition to the dramatic D6D inhibitory effects, administration of SC-26196 at 100 mpk/d for 4 wks consistently resulted in significant hepatomegaly in all animal models tested. It is unclear whether this toxicity is a result of its metabolism, an inhibitory effect on CYP450 enzymes, or other direct effects on liver physiology. However, there is some evidence to suggest that SC-26196 may act on another microsomal liver enzyme that could explain its hepatotoxicity.

Potential off-target effects on microsomal triglyceride transfer protein (MTP) may also be a concern. MTP is a liver enzyme that transfers triglycerides to apoB100, thereby playing critical role in hepatic VLDL synthesis and release. MTP inhibitors (MTPIs) represent a novel class of potent anti-hyperlipidemic agents through their inhibitory effect on hepatic VLDL synthesis/release, but their clinical utility is limited by hepatosteatosis (fatty liver) resulting from an accumulation of triglycerides and immature VLDL particles in liver. Given the potent hypolipidemic effects of SC-26196 in LDLR−/− mice and its hepatotoxicity, the possibility that SC-26196 might exhibit MTP inhibiting properties was examined. SC-26196 inhibited MTP activity in purified bovine MTP and rat liver microsomal extracts at a 100 mpk dosing in vivo, albeit with relatively weak potency. This weak inhibition of MTP may explain the heptatotoxicity of SC-26196 that limits its potential as a therapeutic agent in humans. A SC-26196 derivative may be developed that could represent an orally active D6D inhibitor without this off-target effect.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhibition of D6D Ameliorates Cardiometabolic Disease in Mice

To assess the effects of D6D inhibition on structures and processes related to cardiometabolic diseases and disorders, the following experiments were conducted. Animal studies have reported evidence of increased D6D activity in rodent models of CMD (e.g., increase in AA/LA in tissue phospholipids), making them reasonable models for studying the role of D6D in its pathogenesis. To probe the effect of D6D directly, the compound SC-26196, a selective D6D inhibitor was orally administered by admixing the SC-26196 in the food mixtures of the rodent models of CMD at a dosage of about 100 mg/kg/day for four weeks. The rodent models of CMD used in these experiments included a murine model of hyperphagic obesity (leptin-deficient ob mice) and a diet-induced insulin resistance model (normal C57Bl/6 mice fed a high-fat "Western" diet) for 8 weeks prior to participation in any experiments.

Figure 3:
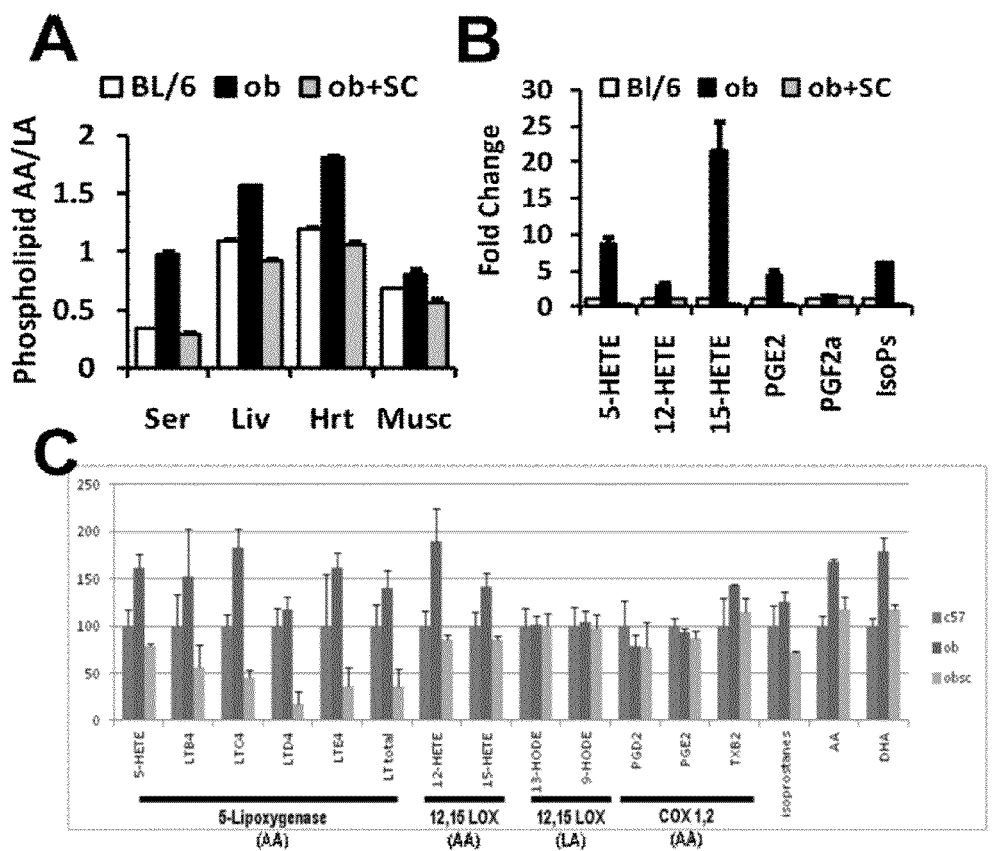
FIGS. 3A-3C are graphs illustrating the effect of D6D inhibition on phospholipid AA/LA ratio of serum, liver, heart and muscle tissue (FIG. 3A), eicosanoid accumulation in the serum (FIG. 3B) and eicosanoid accumulation in cardiac tissues (FIG. 3B) in ob mice maintained on a normal low fat/sucrose chow diet+/− the D6D inhibitor SC-26196 (100 mg/kg/d; 4 weeks).
Figure 7:
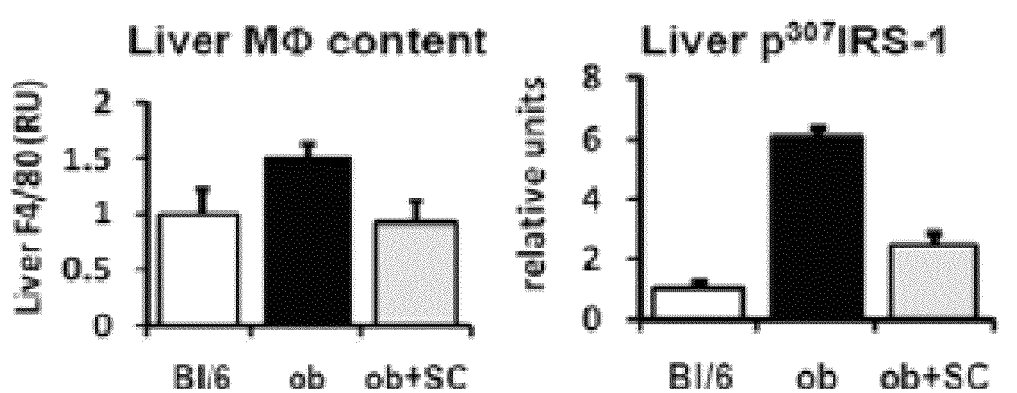
FIG. 7 contains bar graphs illustrating the effect of treatment with a D6D activity inhibiting compound (SC-26196) on reduced hepatic macrophage content and ser-307 phosphorylation of IRS-1 on hyperphagic obese/insulin resistant ob mice maintained on a normal (low fat/sucrose diet).
Figure 8:
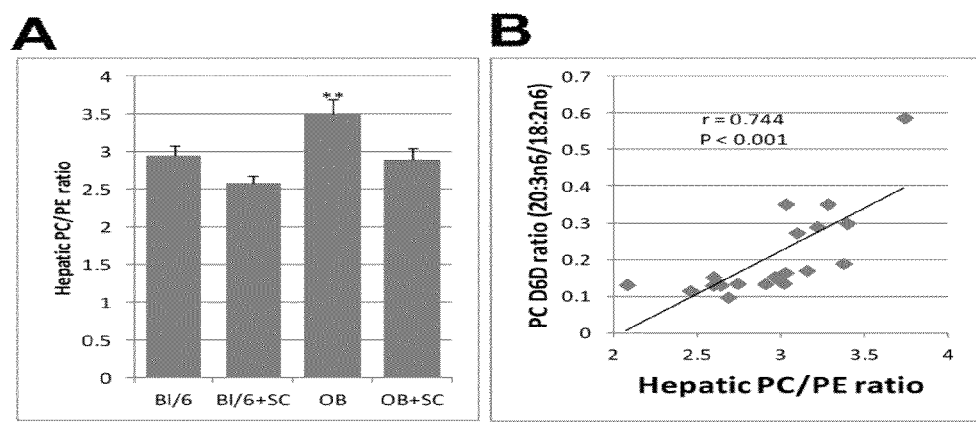
FIG. 8 contains bar graphs illustrating the effect of treatment of hyperphagic obese/insulin resistant ob mice maintained on a normal (low fat/sucrose diet) with the D6D inhibitor Sc-26196 (100 mg/kg/d; 4 weeks) on hepatic PC/PE ratio and cardiac phospholipid/cardiolipin composition.
Figure 9:
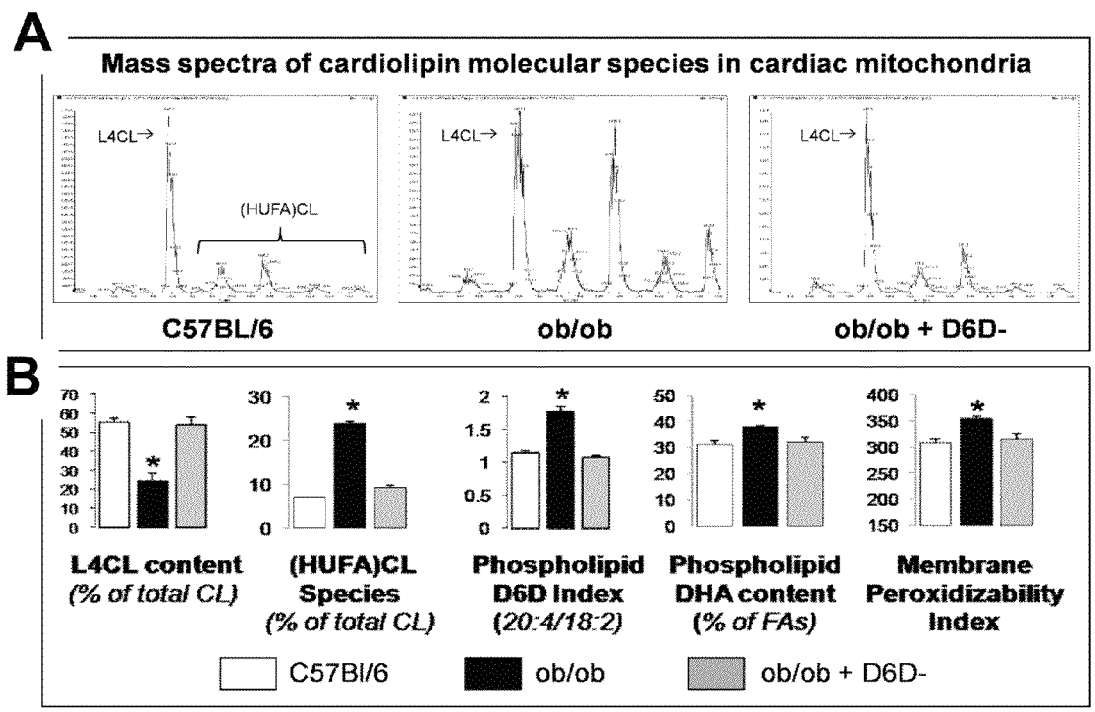
FIG. 9A contains mass spectra graphs of cardiolipin molecular species in cardiac mitochondria for 4 month old ob/ob mice administered the selective D6D inhibitor SC-26196 (100 mg/kg/d mixed in chow) for 4 weeks (ob/ob+ D6D−; n=12) compared to lean C57Bl/6 receiving no treatment.
FIG. 9B are bar graphs summarizing the effect of treatment with the D6D inhibitor on the cardiac cardiolipin profile, phospholipid D6D activity index (20:4/18:2 ratio), phospholipid DHA content, and the membrane peroxidizability index (calculated as [(% 18:2X1)+(% 20:4×4)+(% 22:6X8)]) in ob/ob mice to levels similar to those in lean age-matched control mice (C57Bl/6).
Figure 10:
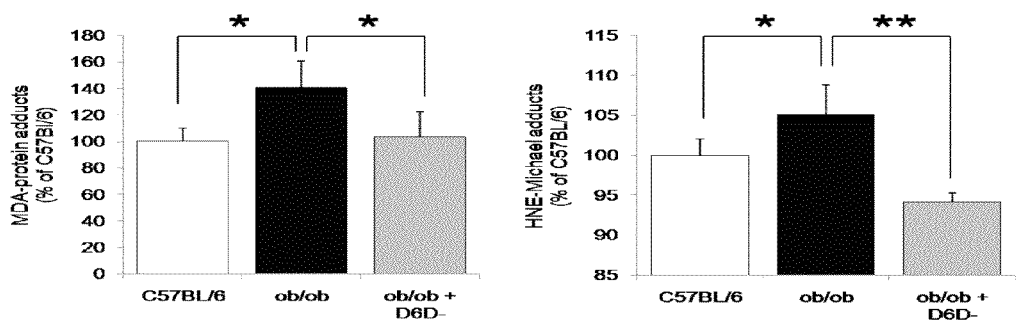
FIG. 10 contains bar graphs summarizing the effects of the treatment of 4 month old ob/ob mice administered the selective D6D inhibitor SC-26196 compared to lean C57Bl/6 receiving no treatment on myocardial abundance of proteins cross-linked by the lipid peroxidation products MDA (malondialdehyde, derived from n−3 PUFAs) and HNE (4-hydroxynonenal, derived from n−6 PUFAs).

Initially, the effects of D6D inhibition in conjunction with a normal diet were assessed. 4 mo old ob/ob mice were administered the selective D6D inhibitor SC-26196 (100 mg/kg/d mixed in chow) for 4 weeks (ob/ob+D6D−; n=12). The ob mice treated with SC-26196 for four weeks (ob+SC) were compared to untreated ob mice (ob) and normal C57Bl/6 mice (Bl/6). FIGS. 3A-C summarizes the results of this comparison. Treatment with SC-26196 reversed significant elevations in phospholipid AA/LA ratio of serum, liver, heart and muscle tissue (FIG. 3A), and abolished significant increases in several eicosanoid species in serum (FIG. 3B) and heart tissue (FIG. 3C). As summarized in FIG. 7, treatment with SC-26196 normalized responses to a glucose tolerance test, decreased serum insulin, and reduced hepatic macrophage (MΦ) content and ser-307 phosphorylation of IRS-1, the canonical cellular mechanism of hepatic insulin resistance resulting from inflammatory signaling. As summarized in FIGS. 8A and 8B, treatment with SC-26196 reduced the hepatic PC/PE ratio in the treated ob mice. FIG. 9 illustrates that SC-26196 treatment normalized the cardiac phospholipid/cardiolipin composition in the treated ob mice. SC-26196 treatment also reduced cardiac oxidative stress in ob mice as summarized in FIG. 10.

D6D inhibition did not ablate tissues of long-chain PUFAs, but instead decreased the long-chain PUFAs to control levels, suggesting the existence of redundant mechanism for maintaining basal levels of LC-PUFAs for essential biological functions. There are important physiological functions of LC-PUFA (including AA) that can presumably remain intact despite pharmacological D6D inhibition.

Figure 4:
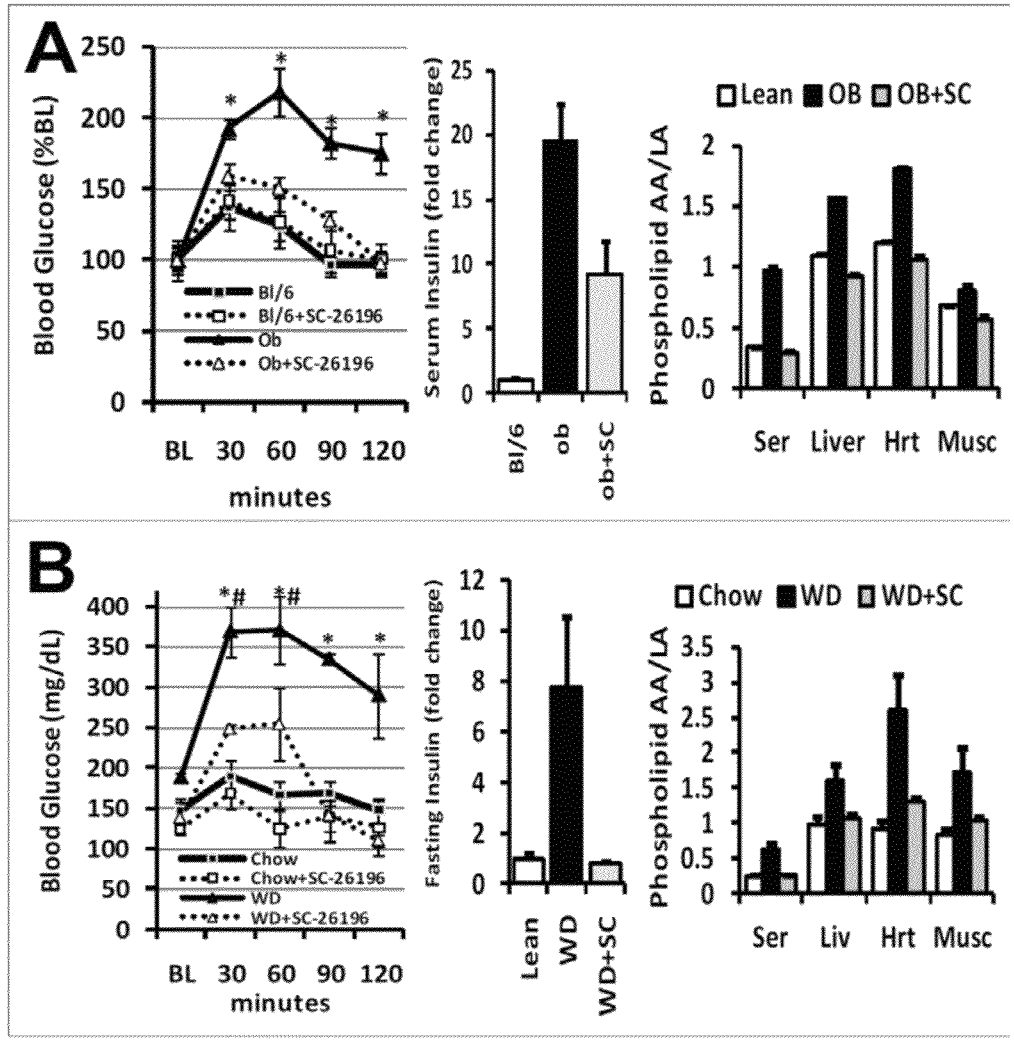
FIG. 4A contains graphs illustrating the effect of treatment with a D6D activity inhibiting compound (SC-26196) on tolerance to a glucose challenge (1 gpk, i.p.), fed/fasting serum insulin levels, and tissue phospholipid AA/LA ratio in ob mice.
FIG. 4B contains graphs illustrating the effect of treatment with a D6D activity inhibiting compound (SC-26196) on tolerance to a glucose challenge (1 gpk, i.p.), fed/fasting serum insulin levels, and tissue phospholipid AA/LA ratio in C57Bl/6 mice fed a high fat/sucrose "western" diet (WD).

To assess the interaction of a high-fat Western diet with the effects of D6D inhibition, the following experiment was conducted. The ob mice and the Bl/6 mice were maintained on a high fat/sucrose Western diet and part of each group was treated with SC-26196 in a similar manner as described above. The treated and untreated ob and Bl/6 mice were compared. FIGS. 4A-4B summarize the results of this experiment. The treatment of the ob mice with SC-26196 reduced fasting blood glucose (BL), normalized responses to a glucose tolerance test and normalized 8-fold elevations in serum insulin levels, as summarized in FIG. 4A. Similar results were observed for the Bl/6 mice, as summarized in FIG. 4B.

Figure 5:
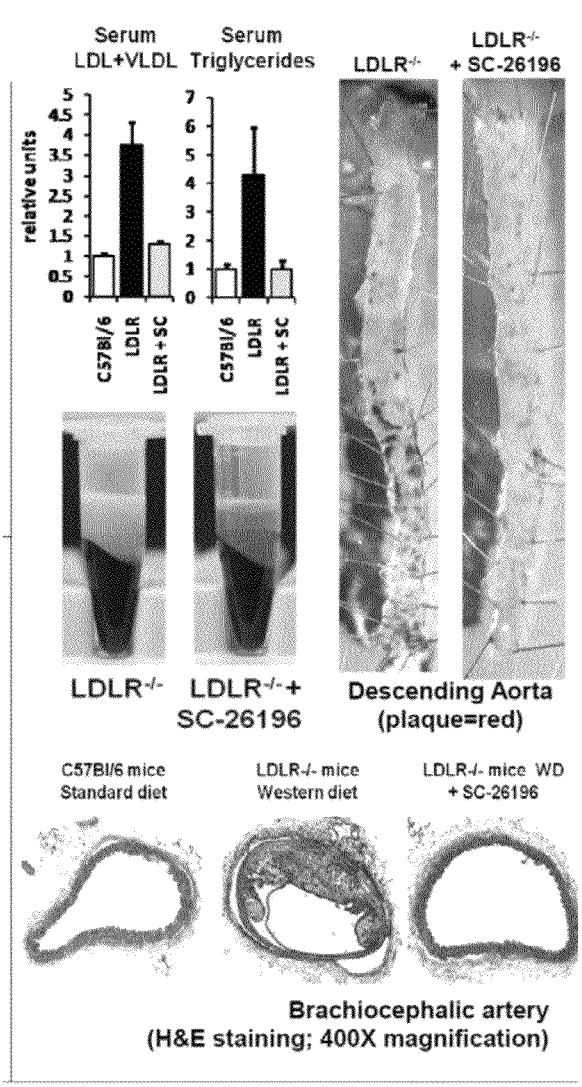
FIG. 5 contains graphs and images illustrating the effect of treatment with a D6D activity inhibiting compound (SC-26196) on hyperlipidemia, atherosclerosis in mice lacking LDL receptors fed high fat/sucrose "western" diet (LDLR−/−).
Figure 6:
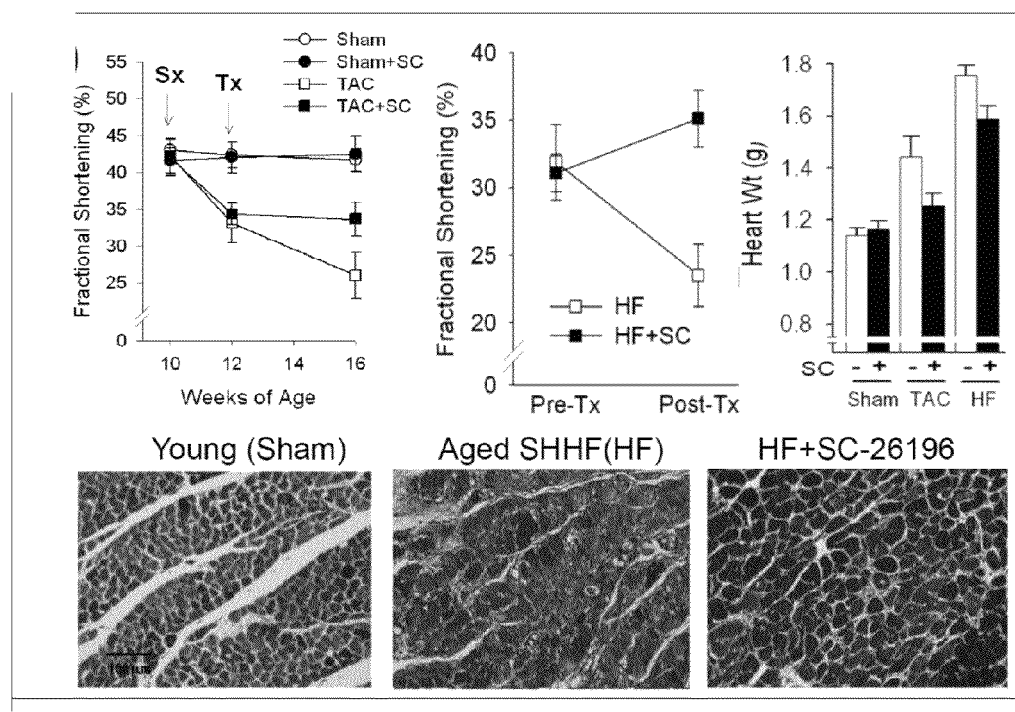
FIG. 6 contains graphs and images illustrating the effect of treatment with a D6D activity inhibiting compound (SC-26196) on cardiac dysfunction, pathologic hypertrophy and fibrosis in rats subjected to thoracic aortic banding (TAC) or chronic hypertension (HF).

Mice lacking LDL receptors (LDLR −/−) were similarly maintained on a high fat/sucrose Western diet and treated with SC-26196 in a similar manner as described above. As summarized in FIG. 5, SC-26196 treatment ameliorated hyperlipidemia and atherosclerosis in mice lacking LDL receptors fed the Western diet. The treatment also attenuated cardiac dysfunction, pathologic hypertrophy and fibrosis in mice subjected to thoracic aortic banding (TAC) or chronic hypertension (HF), as summarized in FIG. 6.

The results of this experiment demonstrated that D6D inhibition reversed elevations in D6D activity indices (e.g., AA/LA ratio) in serum, liver, heart and muscle in these models, and also normalized glucose tolerance and serum levels of several COX and LOX-derived proinflammatory eicosanoids; attenuated hepatic inflammation (macrophage content) and insulin receptor inactivation (IRS-1 phosphorylation); and reduced evidence of tissue lipoxidative stress.

Example 2

Generation of Fads2 Transgenic Mice

To develop and characterize a transgenic mouse with global over-expression of the D6D gene, Fads2, the following experiments were conducted.

Figure 15:
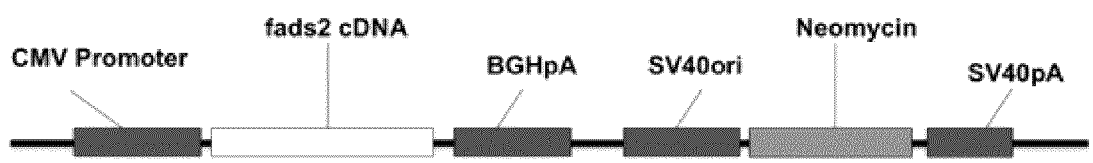
FIG. 15 is a schematic view of the expression cassette used to develop the Fads2-TG transgenic mice.

A full length mouse Fads2 cDNA sequence (1.6 kb) was cloned into the EcoRV and NotI site of the pcDNA-3.1(+) mammalian expression vector as illustrated schematically in FIG. 15. In this vector, Fads2 was placed downstream of a CMV promoter and upstream of a polyadenylation sequence (BGHpa) and neomycin resistant gene. To generate transgenic mice over-expressing Fads2, a purified ~4.6 kb NruI/

Bst1107I fragment containing the CMV-Fads2 expression cassette, was microinjected into pronuclei of fertilized FVB/N mice.

Figure 16:
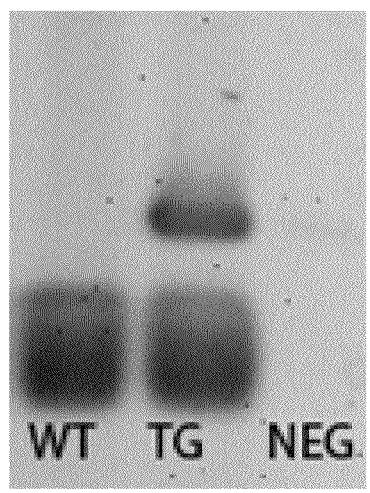
FIG. 16 is a Southern blot image of transgenic expression from tail tissue of Fads2-TG transgenic mice (TG) compared to wild-type (WT) mice.

Transgenic positive founder mice were identified by Southern blot and PCR amplification of genomic DNA isolated from the tail. An image of a representative Southern blot comparing wild type (WT), transgenic (TG), and a negative control (NEG) is provided in FIG. 16.

Figure 17:
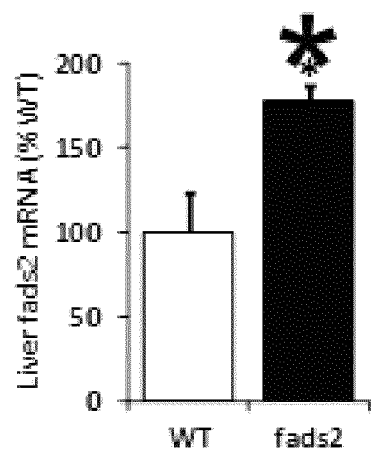
FIG. 17 is a bar graph summarizing Fads2 mRNA expression of Fads2-TG transgenic mice (TG) compared to wild-type (WT) mice.
Figure 18:
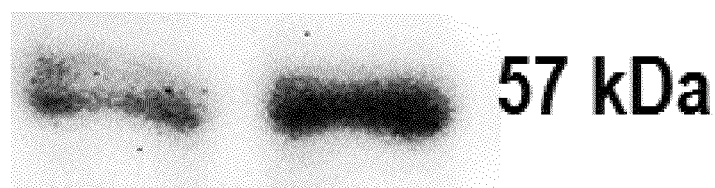
FIG. 18 is a blot image of liver D6D protein expression in Fads2-TG transgenic mice (TG) compared to wild-type (WT) mice.
Figure 19:
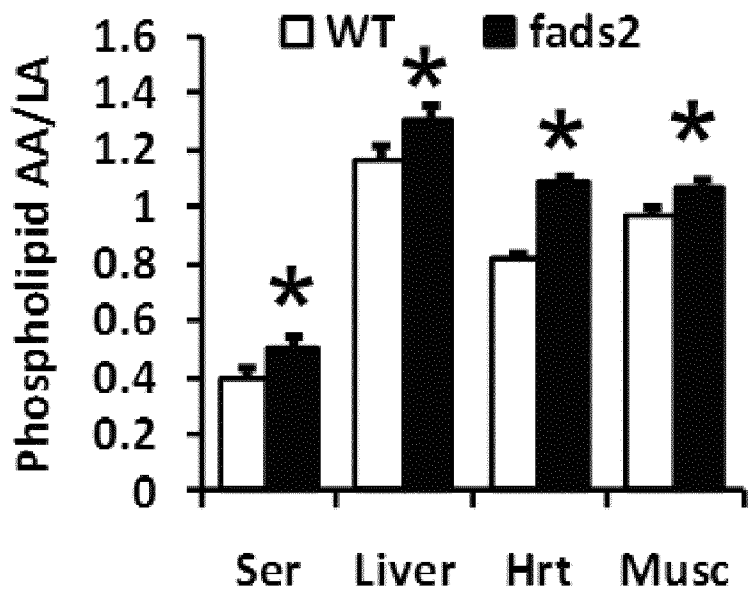
FIG. 19 is a bar graph summarizing D6D PUFA product/precursor ratios in multiple tissues of the F4 generation of Fads2-TG transgenic mice (fads2) compared to wild-type (WT) mice.

Independent founders were used to establish CMV-Fads2 transgenic mouse lines that were tested for Fads2 expression levels in the heart, liver and other tissues of interest. At approximately 6 weeks of age, transgenic positive (TG) mice were mated to wild-type mice to assess germline transmission according to standard procedures, and the offspring were crossbred for at least six generations. FIG. 17 is a bar graph comparing Fads2 mRNA expression for the wild-type (WT) and the transgenic CMV-Fads2 mice (fads2), illustrating that the fads2 mice have demonstrated consistent and persistent D6D overexpression at the mRNA level. FIG. 18 is a Southern blot comparing Fads2 protein expression for the wild-type (WT) and the transgenic CMV-Fads2 mice (Fads2), illustrating that the Fads2 mice have demonstrated consistent and persistent D6D overexpression at the protein level. FIG. 19 is a set of bar graphs comparing the AA/LA ratio within serum, liver, cardiac, and muscle tissues, illustrating that the fads2 mice consistently exhibited the anticipated increases in D6D product/precursor ratios in tissue phospholipids.

The results of this experiment demonstrated the development of a Fads2 transgenic mouse with stable and consistent phenotypic properties across at least five or more generations.

Example 3

Overexpression of D6D Increases Fasting Glucose and Impairs Glucose Tolerance

To assess the consequences of D6D overexpression in processes and structures related to cardiometabolic disease and disorders, the following experiments were conducted. A line of mice with transgenic overexpression of the D6D gene (fads2) were developed using the methods summarized in Example 2

Figure 14:
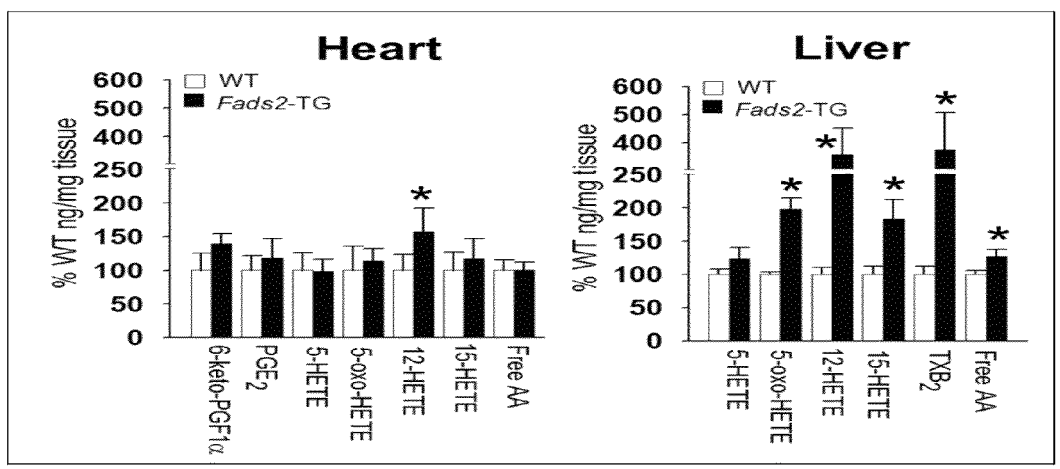
FIG. 14 is a bar graph illustrating the effect of transgenic overexpression of the D6D gene (fads2; F1 heterozygotes) compared to wild-type (WT) littermates on eicosanoids in liver and heart.

Phenotyping studies of the first-fifth generation of fads2-TG mice at 3-4 months of age were performed to characterize a number of structures related to cardiometabolic disease and disorders that may be related to D6D hyperactivity. Corresponding measurements were performed on wild-type (WT) littermates to assess differential effects due to D6D overexpression. As summarized in FIG. 21, fads2 overexpression impaired glucose tolerance, increased AA/LA ratio in serum, liver, heart, and muscle tissues, and increased fads2 mRNA expression to levels comparable to ob mice (ob) or Western diet-induced cardiometabolic disease (WD). The fads2-TG mice exhibited also exhibited elevated cardiac and hepatic eicosanoid levels (FIG. 14); only minor evidence of eicosanoid accumulation was observed in cardiac tissues, while 2-4 fold increases in several species were evident in liver tissues.

Figure 11:
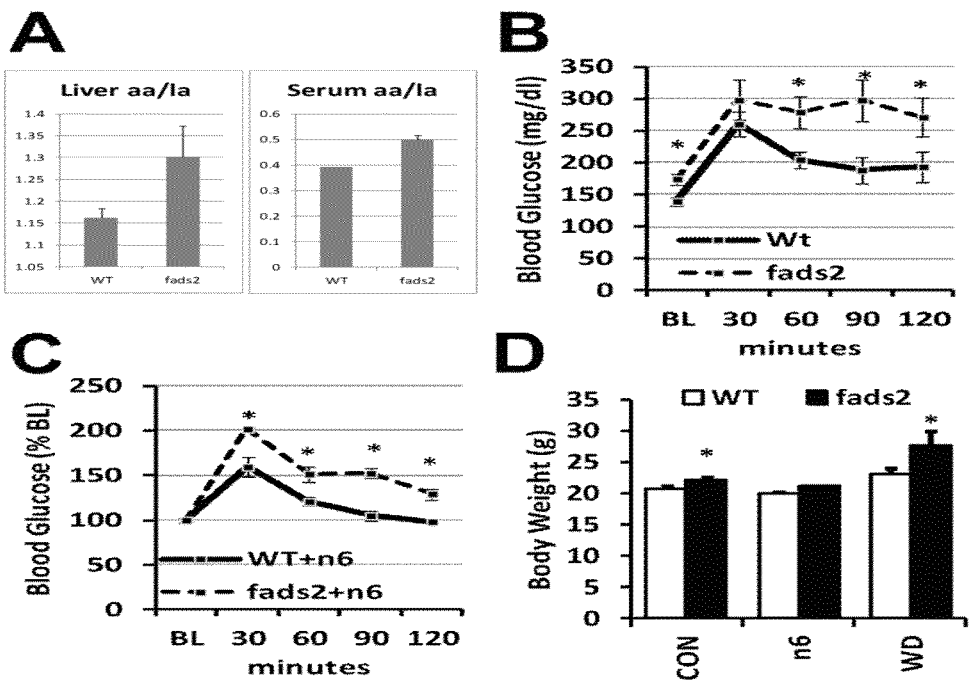
FIGS. 11A-D contains graphs summarizing the effect of transgenic overexpression of the D6D gene (fads2; F1 heterozygotes) compared to wild-type (WT) littermates on: AA/LA ratio of hepatic and serum phospholipids (FIG. 11A); fasting hyperglycemia and glucose intolerance (FIG. 11B), glucose intolerance after 4 weeks of dietary LA supplementation (5% soybean oil added to diet (FIG. 11C); and increased weight gain vs. wild-type littermates (FIG. 11D). *P<0.05 vs. WT; N=4-6/group FIG. 12 is a bar graph illustrating the effect of transgenic overexpression of the D6D gene (fads2; F1 heterozygotes) compared to wild-type (WT) littermates on hepatic phosphatidylcholine/phosphatidylethanolamine (PC/PE) ratio Fads2-TG mice as assessed by normal phase liquid chromatography.
Figure 12:
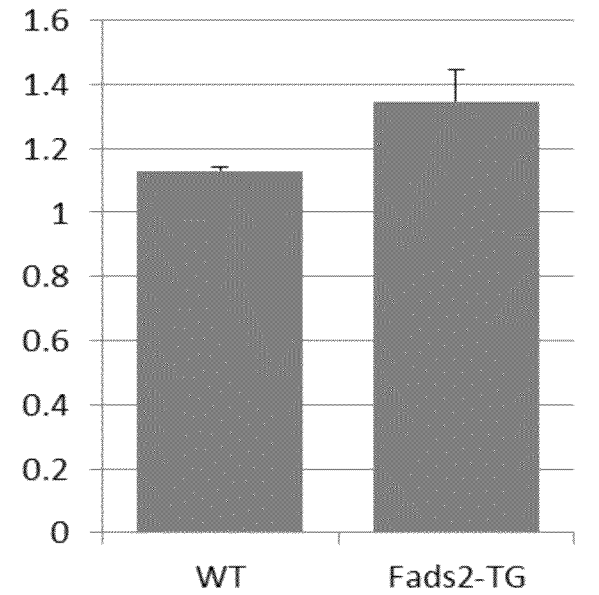
Figure 13:
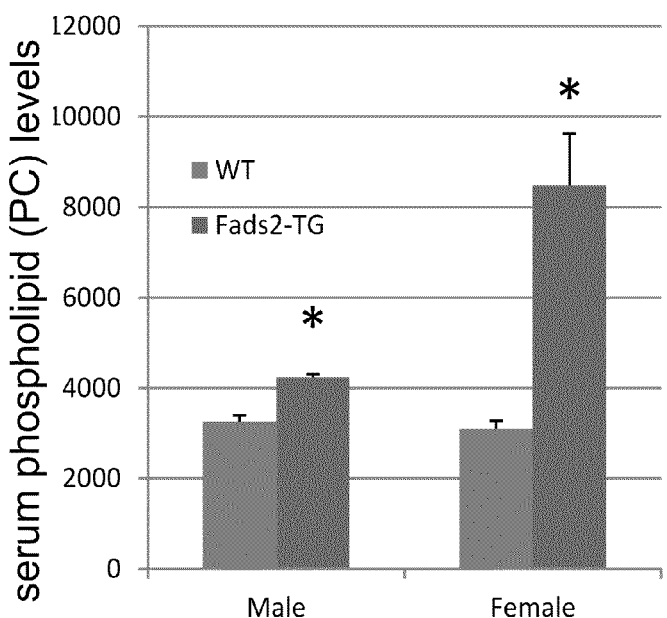
FIG. 13 is a bar graph illustrating the effect of transgenic overexpression of the D6D gene (fads2; F1 heterozygotes) compared to wild-type (WT) littermates on serum phospholipid (PC).

PC/PE levels (FIG. 12 and FIG. 20), and hyperlipidemia (FIG. 13) were increased in the fads2-TG mice, providing strong direct support for a role of D6D in glucose intolerance/metabolic disease. Supplementing the diet with LA-rich soybean oil (5% w/w) exacerbated glucose intolerance in the fads2+/− mice, but not wild-type mice as shown in FIG. 11C, supporting the interaction of D6D with LA in the modern diet in the production of the insulin resistant phenotype. Finally, fads2+/− mice fed a high fat/sucrose "western" diet for 3 weeks exhibited greater weight gain (FIG. 11D). and glucose intolerance compared to wild-type littermates that were only mildly affected.

Compositional analysis of individual phospholipid classes in the heart revealed a pattern of PUFA redistribution generally consistent with expectations. FIG. 18 summarizes the PUFA contents of the major myocardial phospholipid species phosphatidylcholine (PC), -ethanolamine (PE), -inositol (PI) and cardiolipin (CL) from male 4 month old F4 wild-type (white bars) and Fads2-TG (black bars) (n=8/group). The Fads2-TG mouse exhibited a dramatic 2-fold increase in AA at the expense of DHA in phosphatidylinositol (PI), which is known to be a primary source of AA for eicosanoid synthesis.

Figure 20:
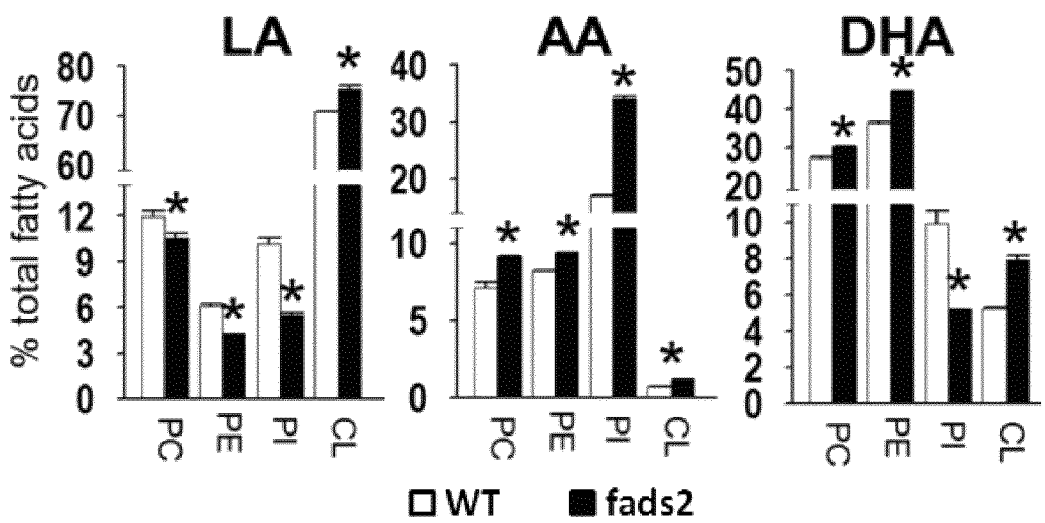
FIG. 20 contains bar graphs summarizing PUFA contents of the major myocardial phospholipid species phosphatidylcholine (PC), -ethanolamine (PE), -inositol (PI) and cardiolipin (CL) from F4 wild-type mice (white bars) and Fads2-TG transgenic mice (black bars).

FIG. 20 is a bar graph summarizing the results of echocardiographic imaging of the F3-F5 of wild-type mice (white bars) and Fads2-TG mice (black bars). Compared to wild-type mice (WT), the Fads2-TG mice exhibited larger LV diameters (LVID) and lower fractional shortening (LV FS) by 4 months of age, as illustrated in FIG. 20. The Fads2-TG mice also exhibited slightly higher heart weights, although these differences were not significant and were well within a normal range. Further, despite significant increases in the double bond content of phospholipids as measured by membrane peroxidizability, only a slightly elevated cardiac MDA content was observed in the Fads2-TG mice.

The results of this experiment demonstrated that D6D overexpression in the fads2 transgenic mice result in comparable phenotypic characteristics to other animal models of cardiometabolic disorders.

What is claimed is:

1. A method for identifying a test compound as a candidate compound for the treatment of a cardiometabolic disease or disorder in a mammal by inhibition of delta-6 desaturase, the method comprising a) contacting a mammalian delta-6 desaturase (D6D) with the test compound; b) determining a change in the level of at least one index of D6D activity in the presence of the test compound, wherein the at least one index of D6D activity is selected from the arachidonic acid/linoleic acid (AA/LA) ratio, or the level of a proinflammatory eicosanoid; and c) determining a change in the level of at least one index of a cardiometabolic disease-related disorder, wherein the at least one index of the cardiometabolic disease-related disorder is selected from any one or more of: blood or serum glucose level, glucose tolerance, blood or serum insulin level, insulin resistance, liver macrophage content, or insulin receptor inactivation (IRS-1 phosphorylation); wherein a decreased level of D6D activity and a decreased level of a cardiometabolic disease-related disorder in the presence of the test compound relative to a level of D6D activity and a level of a cardiometabolic disease-related disorder in the absence of the test compound identifies the test compound as a candidate compound for the treatment of a cardiometabolic disease or disorder in a mammal.

2. A method according to claim 1, wherein contacting the mammalian D6D with the test compound comprises administering an amount of the candidate compound to a mammal, and determining a change in the level of the at least one index of D6D enzymatic activity and a change in the level of the at least one index of a cardiometabolic disease-related disorder in the presence of the test compound comprises: determining a first value of at least one index of D6D enzymatic activity and a first value of at least one index of the cardiometabolic disease-related disorder before the administration of the candidate compound to the mammal; maintaining the mammal for a time and under conditions sufficient to allow the candidate compound to modify D6D enzymatic activity in the mammal; determining a second value for the at least one index of D6D activity and a second value for the at least one index of the cardiometabolic disease-related disorder after the administration of the candidate compound to the mammal; comparing the first value and the second value of the at least one index of D6D enzymaticactivity, wherein a reduced second value relative to the first value is indicative that the candidate compound reduces D6D enzymatic activity in vivo; and comparing the first value and the second value of the at least one index of the cardiometabolic disease-related disorder, wherein a reduced second value relative to the first value is indicative that the candidate compound reduces cardiometabolic disease or disorder in vivo.

3. A method according to claim 2, wherein the at least one index of D6D activity is determined from a first tissue measurement and a second tissue measurement taken from a tissue selected from any one or more of: serum, liver, heart or muscle.

4. A method according to claim 2, wherein the mammal is an animal model of human cardiometabolic disease.

5. A method according to claim 2, wherein the mammal is a murine model of hyperphagic obesity comprising a leptin-deficient ob mouse.

6. A method according to claim 2, wherein the mammal is a murine model of diet-induced insulin resistance comprising a normal mouse maintained on a fat-enriched ("western") diet for a period of at least about 12 weeks.

7. A method according to claim 2, wherein the mammal is a transgenic mouse which overexpresses the fatty acid desaturase 6 (fads2) gene.

8. A method according to claim 1, wherein the cardiometabolic disease-related disorder is selected from any one or more of: hyperglycemia, type 2 diabetes, metabolic syndrome, hyperlipidemia, chronic inflammation, or oxidative stress.

* * * * *